US008664424B2

(12) United States Patent
Wang et al.

(10) Patent No.: US 8,664,424 B2
(45) Date of Patent: Mar. 4, 2014

(54) METHOD FOR PREPARING 2,5-DIMETHYLPHENYLACETIC ACID

(75) Inventors: Ping Wang, Taizhou (CN); Xiaobin Fan, Taizhou (CN); Xingjun Lin, Taizhou (CN); Zhaohui He, Taizhou (CN)

(73) Assignees: Lianhe Chemical Technology Co., Ltd, Zhejiang (CN); Jiangsu Lianhe Chemical Technology Co., Ltd., Jiangsu (CN)

( * ) Notice: Subject to any disclaimer, the term of this patent is extended or adjusted under 35 U.S.C. 154(b) by 0 days.

(21) Appl. No.: 13/642,808

(22) PCT Filed: Jun. 7, 2011

(86) PCT No.: PCT/CN2011/075370
§ 371 (c)(1),
(2), (4) Date: Oct. 22, 2012

(87) PCT Pub. No.: WO2012/122747
PCT Pub. Date: Sep. 20, 2012

(65) Prior Publication Data
US 2013/0046108 A1 Feb. 21, 2013

(30) Foreign Application Priority Data
Mar. 13, 2011 (CN) .......................... 2011 1 0060598

(51) Int. Cl.
C07C 69/76 (2006.01)
C07C 51/10 (2006.01)
C07C 22/04 (2006.01)
C07D 293/04 (2006.01)
C07C 57/30 (2006.01)

(52) U.S. Cl.
USPC ............... 560/8; 562/406; 570/191; 570/193; 570/194; 570/257; 570/258; 548/100; 548/335.1; 564/281

(58) Field of Classification Search
None
See application file for complete search history.

(56) References Cited

U.S. PATENT DOCUMENTS

| | | | | | |
|---|---|---|---|---|---|
| 3,969,239 | A | * | 7/1976 | Shinohara et al. | 210/735 |
| 3,988,358 | A | * | 10/1976 | Heck | 558/353 |
| 4,654,436 | A | * | 3/1987 | Lane et al. | 560/80 |
| 4,668,816 | A | * | 5/1987 | Epstein | 560/105 |
| 4,713,484 | A | * | 12/1987 | Epstein | 562/406 |
| 5,143,889 | A | * | 9/1992 | Takahiro et al. | 502/427 |
| 5,315,029 | A | * | 5/1994 | Chockalingam | 560/105 |
| 6,555,704 | B1 | * | 4/2003 | Elango | 562/406 |
| 6,653,502 | B2 | * | 11/2003 | Geissler | 560/97 |
| 2005/0049438 | A1 | * | 3/2005 | Hardacre et al. | 568/315 |
| 2008/0234501 | A1 | | 9/2008 | Himmler | |
| 2009/0156839 | A1 | | 6/2009 | Himmler | |

FOREIGN PATENT DOCUMENTS

| | | |
|---|---|---|
| CN | 1918103 A | 2/2007 |
| CN | 101092345 A | 12/2007 |
| CN | 102140062 A | 8/2011 |
| DE | 10 2008 020 361 A1 | 12/2008 |
| JP | A-2008-291008 | 12/2008 |

OTHER PUBLICATIONS

Fang et. al. Blanc Reaction of Aromatic Compounds Catalyzed by Ionic Liquids, Chinese Journal of Chemical Engineering, 16(3) 357-360, 2008.*
Kohlpaintner, C.W., Beller, M., "Palladium-catalyzed carbonylation of benzyl chlorides to phenylacetic acids—a new two-phase process," Journal of Molecular Catalysis A: Chemical, 116, 259-267 (1997).*
Jones, R.V.H., Lindsell, W.E., Palmer, D.D., Preston, P.N., Whitton, A.J., Palladium-catalyzed carbonylation of arylmethyl halides: efficient synthesis of arylacetic acid esters, Tetrahedron Letters, 46, 8695-8697 (2005).*
Sakamoto et al., "Hetera-*p*-carbophanes. III. Conformation of Amide Groups in and Internal Rotation of Diaza[*n*]paracyclophanes with Two Alkoxy Groups at the Benzene Ring," *Bulletin of the Chemical Society of Japan*, vol. 48(2), pp. 497-504, 1975.
Gong et al., "The Research Progress on Carbonylation Synthesis of Phenylacetic acid and its Esters," *Chemistry Online*, vol. 1, pp. 20-25, 1999 (with translation).
Fang et al., "Blanc Reaction of Aromativ Compounds Catalyzed by Ionic Liquids," *Chinese Journal of Chemical Engineering*, vol. 16(3), pp. 357-360, 2008.
Jun. 21, 2012 Chinese Office Action issued in Chinese Patent Application No. 201110060598.X (with translation).
Jun. 21, 2012 Chinese Search Report issued in Chinese Patent Application No. 201110060598X (with translation).
Dec. 15, 2011 International Search Report issued in International Patent Application No. PCT/CN2011/075370 (with translation).

* cited by examiner

Primary Examiner — Johann R Richter
Assistant Examiner — Mark Luderer
(74) Attorney, Agent, or Firm — Oliff PLC

(57) ABSTRACT

Provided is a method for preparing 2,5-dimethylphenylacetic acid, wherein p-xylene is mixed with paraformaldehyde and concentrated hydrochloric acid in a solvent of ion liquid to obtain 2,5-dimethyl benzyl chloride by the chloromethylation reaction. Then, 2,5-dimethyl benzyl chloride is introduced into a reactor with an acid binding agent and a solvent, the carbonylation and hydrolysis reaction is conducted in the presence of a catalyst to obtain 2,5-dimethylphenylacetic acid. The present process has new route, less synthesis steps, simple operation, lower cost, increased yield, and is friendly to the environment. Therefore, the method is suitable for industrial production.

7 Claims, 1 Drawing Sheet

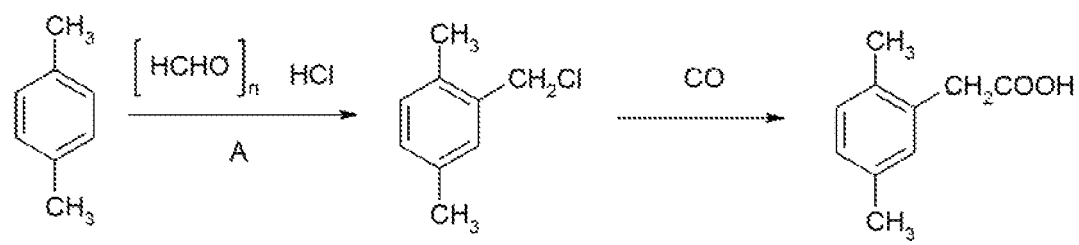

METHOD FOR PREPARING 2,5-DIMETHYLPHENYLACETIC ACID

FIELD OF THE INVENTION

The present invention relates to a chemical synthetic method, especially relates to a method for preparing 2,5-dimethylphenylacetic acid which is an intermediate of fine chemical industry.

BACKGROUND 2,5-Dimethylphenylacetic acid is an important intermediate of fine chemical industry. It is widely used in the fields of medicine and pesticide, and especially, it is a key intermediate of the novel pesticide called spirotetramat which, is the only pesticide with bi-directional systemic transmission function so far.

Several main methods in synthesizing 2,5-dimethylphenylacetic acid referred to the domestic and overseas literatures are as follows:

1. In Bulletin of the Chemical Society of Japan 1975, 48(2), 497-504, the 2,5-dimethylphenylacetic acid was synthesized by a two-step reaction of cyaniding and hydrolyzing with the starting reactant 2,5-dimethylbenzyl chloride by Kazuhiko et al. The synthetic route was as the following:

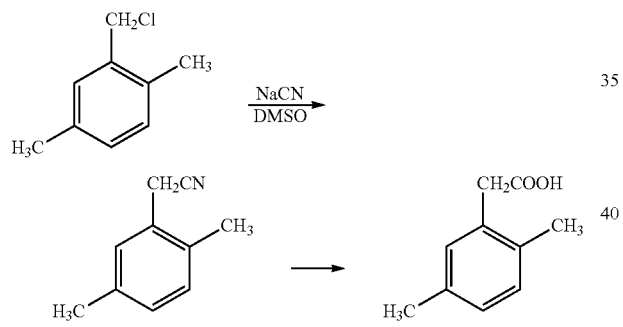

2. The synthetic method of 2,5-dimethylphenylacetic acid which was disclosed, in Bayer's patent CN1918103 was to transform the p-xylene into 2-chloro-1-(2,5-dimethylphenyl)ethanone(I) with chloroacetyl chloride, transform the said ketone into the corresponding ketal(III) with the diol(II), and then rearrange the ketal(III) to give the mixture of 2,5-dimethylphenylacetic acid hydroxyalkyl ester(IV) and bis(2,5-dimethylphenylacetic acid) diester(V). Finally, the said mixture was hydrolyzed to give 2,5-dimethylphenylacetic acid. The synthetic route was as the following:

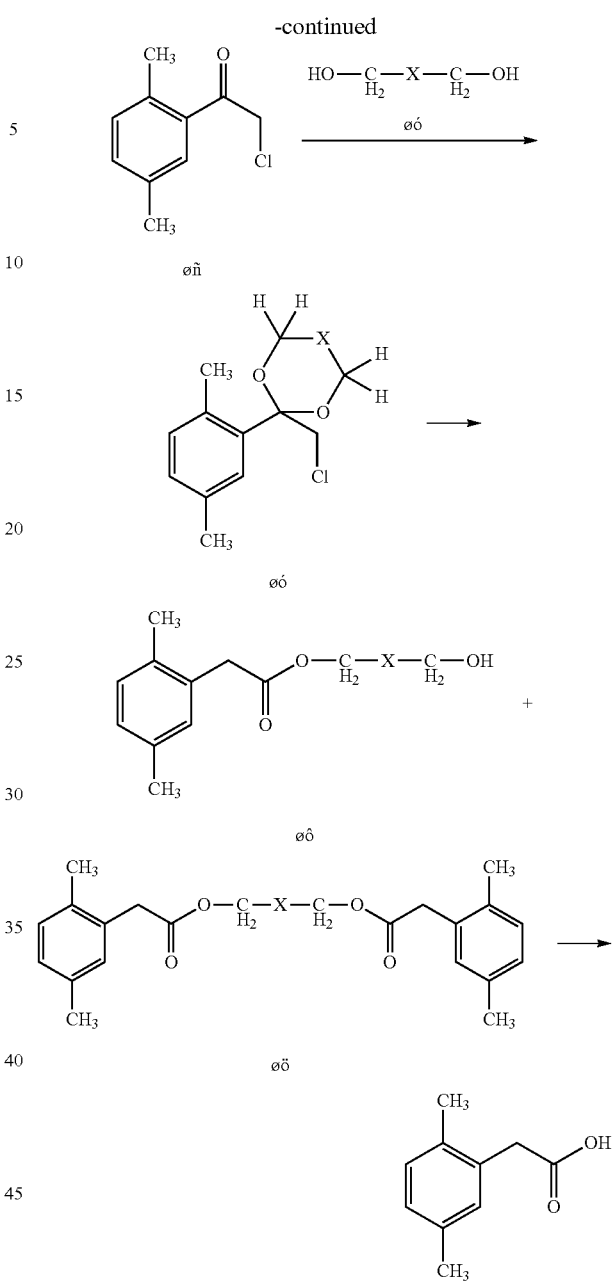

3. A process for preparing 2,5-dimethylphenylacetic acid, in which 2,5-dimethylphenylacetic acid was synthesized by undergoing coupling and hydrolyzing reactions with the starting reactant 1-(2,5-dimethylphenyl)ethanone, was disclosed by Daicel in patent JP2008291008. The synthetic route was as the following:

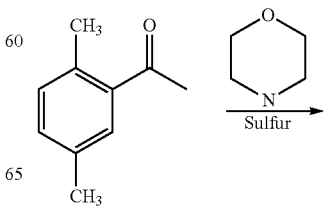

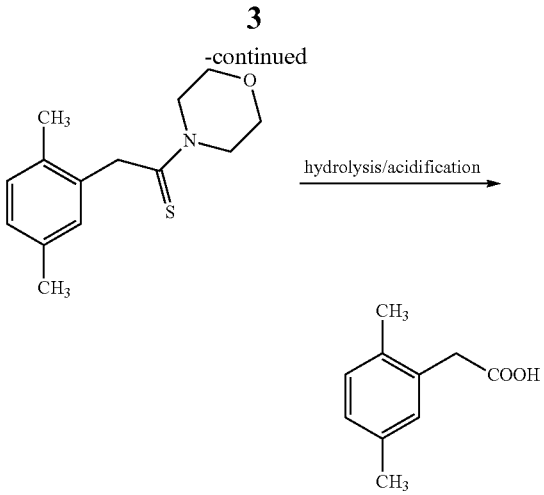

In conclusion, all the processes above have the problems that the raw materials are expensive, synthetic routes are long and the types of reactions are complicated.

DETAILED DESCRIPTION OF THE INVENTION

Therefore, in order to solve the problems of expensive raw materials, long synthetic route and complicated reaction types in the said processes for preparing 2,5-dimethylphenylacetic acid, the present invention provides a novel, convenient, high-yield and environmental friendly method wherein the raw materials are cheap and it is suitable for the industrial production.

The present invention provides a method for preparing 2,5-dimethylphenylacetic acid, which comprises the following steps:

a. chloromethylation reaction: the temperature is raised after the raw material p-xylene, the solvent ionic liquid are mixed with paraformaldehyde and concentrated hydrochloric acid, the chloromethylation reaction proceeds when the gas of hydrogen chloride is inflated, the temperature is kept for 0.5 h after the reaction is completed, the reaction solution is cooled and stands for layering, the organic layer is rectified under vacuum to give 2,5-dimethylbenzyl chloride; wherein the mole ratio of the said p-xylene, paraformaldehyde and ionic liquid is 1:1.1-5:0.01-1, the preferred mole ratio of p-xylene, paraformaldehyde and ionic liquid is 1:1.1-2.0:0.01-0.5.

Furthermore, in the said chloromethylation reaction, the solvent is substituted imidazole ionic liquid in which the cation is imidazole ion and the anion is halogen ion, trifluoromethanesulfonate ion, tetrafluoroborate ion or hexafluorophosphate ion; including 1-butyl-3-methylimidazolium chloride, 1-butyl-3-methylimidazolium bromide, 1-butyl-3-methylimidazolium tetrafluoroborate, 1-butyl-3-methylimidazolium hexafluorophosphate, 1-butyl-3-methylimidazolium trifluoromethanesulfonate, 1-ethyl-3-methylimi-dazolium tetrafluoroborate, 1-ethyl-3-methylimidazolium hexafluorophosphate, 1-hexyl-3-methylimidazolium tetrafluoroborate, 1-hexyl-3-methylimidazolium hexafluorophosphate, 1-octyl-3-methylimidazolium chloride, 1-octyl-3-methylimidazolium bromide, 1-octyl-3-methylimi-dazolium tetrafluoroborate or 1-octyl-3-methylimidazolium hexafluoro phosphate.

Furthermore, the ionic liquid gained by dehydrating the water layer under vacuum which (the water layer) is provided by standing for layering the reaction solution of the completed chloromethylation reaction may be recycled and reused.

b. The temperature is raised after the said 2,5-dimethylbenzyl chloride, acid binding agent and solvent are put into the reactor with the presence of catalyst, the carbonylation and hydrolyzation reactions proceed when the gas of carbon monoxide is inflated, after the reaction is completed, the reaction solution is cooled, then liquid caustic soda is added under the protection of nitrogen, the reaction solution is stirred for 1 h, standing and layering, 36% hydrochloric acid is added, into the water layer until pH=1, then it is kept warm for 1 h, filtered and dried to provide 2,5-dimethylphenylacetic acid.

Furthermore, in the said carbonylation and hydrolyzation reactions, the catalyst is palladium compound catalyst. The said palladium compound catalyst is selected from palladium chloride, palladium acetate, palladium sulfate, palladium nitrate, palladium oxide, dichlorodiamminepalladium, tetraammine dichloropalladium(II), tetrakis(triphenylphosphine)palladium(0), palladium(II)bis(triphenylphosphine) diacetate, palladium(II)bis(triphenyl-phosphine) dichloride or palladium hydroxide. In the said carbonylation and hydrolyzation reactions, the palladium compound catalyst is preferably selected from tetfakis(triphenylphosphine)palladium(0), palladium(II)bis-(triphenyl-phosphine) diacetate or palladium (II)bis(triphenylphosphine) dichloride.

In the said carbonylation and hydrolyzation reactions, the acid binding agent is organic base or inorganic base. The organic base is selected from one out of pyridine, triethylamine, alkali alcoholate, lithium alkylide or lithium amide compound. The inorganic base is selected from alkali hydroxide, alkali carbonate or bicarbonate, acetate. The said alkali alcoholate is selected from one out of sodium methoxide, potassium ethoxide or potassium t-butoxide. The lithium alkylide is selected from butyllithium or phenyl lithium. The said lithium amide is selected from lithium diisopropylamide (LDA) or Lithium hexamethyldisilazide(LiHMDS). The said alkali hydroxide is selected from sodium hydroxide or potassium hydroxide. The alkali carbonate and bicarbonate are selected from sodium carbonate, potassium carbonate, sodium bicarbonate or potassium bicarbonate. The said acetate is selected from sodium acetate or potassium acetate. The said acid binding agent is preferably selected from pyridine or triethylamide.

The solvent of the said carbonylation and hydrolyzation reactions is selected from ester, ether, alcohol, arenes or nitrile, or the mixture of several of them. The said ester is selected from one out of methyl acetate, ethyl acetate or butyl acetate. The said ether is selected from one out of ethyl ether, methyl t-butyl ether, tetrahydrofuran or p-dioxane. The said alcohol is selected from one out of methanol, ethanol, isopropyl alcohol or tert-pentanol. The said arenes is selected from benzene, toluene or chlorobenzene. The said nitrile is selected from acetonitrile or propionitrile. In the said carbonylation and hydrolyzation reactions, the solvent is preferably selected from isopropyl alcohol or tert-pentanol.

Furthermore, in the said carbonylation and hydrolyzation reactions, the catalyst gained from refiltering after small amount of heavy metal capture agent and flocculant are added to the filtrate may be recycled and reused.

In the reaction formula of the present invention (FIG. 1), paraformaldehyde and concentrated hydrochloric acid are mixed with the solvent A which is substituted imidazole ionic liquid and the raw material p-xylene, to give 2,5-dimethylbenzyl chloride after the chloromethylation reaction. Then 2,5-dimethylbenzyl chloride, acid binding agent and solvent are added into the reactor in the presence of catalyst and 2,5-dimethylphenylacetic acid is provided by undergoing carbonylation and hydrolyzation reactions. Thereby, the method of the present invention has a novel route, reasonable process conditions, short synthetic route, easy operations, high-yield, low cost and less pollution, which has high implementation value and social economic benefits.

DESCRIPTION OF FIGURES

FIG. 1 is the reaction formula of the present invention.

The following examples are illustrative for the present invention, but shouldn't be considered to limit the present invention in any way.

Embodiments

EXAMPLE 1

(1) Chloromethylation reaction 48 g Paraformaldehyde, 106 g p-xylene, 10 g 1-butyl-3-methylimidazolium bromide and 3.2 g concentrated hydrochloric acid whose concentration is 36% are added into a 500 ml four-neck flask and the temperature is raised to 80~85° C. after well stirring. And the reaction solution is kept warm for 0.5 h after the gas of hydrochloride is inflated, and then cooled to the room temperature, standing for layering. The upper layer is organic layer while the lower layer is water layer. The water layer is dehydrated under vacuum and the gained ionic liquid can be recycled and reused. The organic layer is transferred into a 500 ml four-neck flask and is rectified under vacuum. After desolventizing, 139.3 g 2,5-dimethylbenzyl chloride is finally provided (90.1% yield).

(2) Carbonylation and hydrolyzation reactions

To a 1000 ml autoclave, 70.0 g the said rectified 2,5-dimethylbenzyl chloride, 137.5 g triethylamine, 0.3 g palladium(II)bis(triphenylphosphine) dichloride, 81 g water and 168.0 g tert-pentanol are added. Nitrogen is inflated to replace the air for three times and the temperature is raised to 70° C. At 70° C.~75° C., carbon monoxide is inflated until the pressure is not decreasing. After the reaction has finished, it is cooled to 40° C., then the pressure is relieved, and nitrogen is inflated to replace the air for three times again, the reaction solution is transferred into a 1000 ml four-neck flask and then 120.0 g 30% liquid caustic soda is added under the protection of nitrogen, which is stirred for 1 h at 60° C., then standing for layering. The upper layer is organic layer and the lower layer is water layer. 57.6 g 36% hydrochloric acid is added dropwise into the water layer until pH=1. The solution is kept warm for 1 h and filtered, dried under vacuum to give 64.4 g 2,5-dimethylphenylacetic acid (87.2% yield). Finally, small amount of heavy metal capture agent and flocculant can be added into the filtrate and filtered again to give the catalyst. The gained catalyst after filtering can be recycled and reused.

EXAMPLE 2

(1) Chloromethylation reaction 24 g Paraformaldehyde. 53 g p-xylene, 4.9 g 1-ethyl-3-methylimidazolium tetrafluoroborate and 1.6 g concentrated hydrochloric acid whose concentration is 36% are added into a 500 ml four-neck flask and the temperature is raised to 80~85° C. after well stirring. And the reaction solution is kept warm tor 0.5 h after the gas of hydrochloride is inflated, and then cooled to the room temperature, standing for layering. The upper layer is organic layer while the lower layer is water layer. The water layer is dehydrated trader vacuum and the gained ionic liquid can be recycled and reused. The organic layer is transferred into a 500 ml four-neck flask and is rectified under vacuum. Alter desolventizing. 70.6 g 2,5-dimethylbenzyl chloride is finally provided (91.3%) yield).

(2) Carbonylation and hydrolyzation reactions

To a 1000 ml autoclave, 105.0 g the said rectified 2,5-dimethylbenzyl chloride, 206.4 g triethylamine, 0.5 g palladium(II)bis(triphenylphosphine) diacetate, 122 g water and 262.5 g isopropyl alcohol are added. Nitrogen is inflated to replace the air for three times and the temperature is raised to 70° C. At 70° C.~75° C., carbon monoxide is inflated until the pressure is not decreasing. After the reaction has finished, it is cooled to 40° C., then the pressure is relieved, and nitrogen is inflated to replace the air for three times again, the reaction solution is transferred into a 2000 ml four-neck flask and then 180.8 g 30% liquid caustic soda is added under the protection of nitrogen, which is stirred for 1 h at 60° C., then standing for layering. The upper layer is organic layer and the lower layer is water layer. 86.0 g 36% hydrochloric acid is added dropwise into the water layer until pH=1. The solution is kept, warm for 1 h and filtered, dried under vacuum to give 95.7 g 2,5-dimethylphenylacetic acid (85.7% yield). Finally, small amount of heavy metal capture agent and flocculant can be added into the filtrate and filtered again to give the catalyst. The gained catalyst after filtering can be recycled and reused.

EXAMPLE 3

(1) Chloromethylation reaction 36.0 g Paraformaldehyde, 84.8 g p-xylene, 14.0 g 1-butyl-3-methylimi-dazolium chloride and 2.4 g concentrated hydrochloric acid whose concentration is 36% are added into a 250 ml four-neck flask and the temperature is raised to 80~85° C. after well stirring. And the reaction solution is kept warm for 0.5 h after the gas of hydrochloride is inflated, and then cooled to the room temperature, standing for layering. The upper layer is organic layer while the lower layer is water layer. The water layer is dehydrated under vacuum and the gained ionic liquid can be recycled and reused. The organic layer is transferred into a 250 ml four-neck flask and is rectified under vacuum. After desolventizing, 113.4 g 2,5-dimethylbenzyl chloride is finally provided (91.7% yield).

(2) Carbonylation and hydrolyzation reactions

To a 1000 ml autoclave, 92.8 g the said rectified 2,5-dimethylbenzyl chloride, 142.4 g pyridine, 0.5 g palladium(II)bis(triphenylphosphine) diacetate, 108 g water and 222.7 g tert-pentanol are added. Nitrogen is inflated to replace the air for three times and the temperature is raised to 70° C. At 70° C.~75° C., carbon monoxide is inflated until the pressure is not decreasing. After the reaction has finished, it is cooled to 40° C., then the pressure is relieved, and nitrogen is inflated to replace the air for three times again, the reaction solution is transferred into a 1000 ml four-neck flask and then 160 g 30% liquid caustic soda is added under the protection of nitrogen, which is stirred for 1 h at 60° C., then standing for layering. The upper layer is organic layer and the lower layer is water layer. 76.0 g 36% hydrochloric acid is added dropwise into the water layer until pH=1. The solution is kept warm for 1 h and filtered, dried under vacuum to give 85.1 g 2,5-dimethylphenylacetic acid (86.4% yield). Finally, small amount of heavy metal capture agent and flocculant can be added into the filtrate and filtered again to give the catalyst. The gained catalyst after filtering can be recycled and reused.

EXAMPLE 4

(1) Chloromethylation reaction 42 g Paraformaldehyde, 106 g p-xylene, 3.5 g 1-octyl-3-methylimidazolium chloride and 3.3 g concentrated hydrochloric acid whose concentration is 36% are added into a 500 ml four-neck flask and the temperature is raised to 80~85° C. after well stirring. And the reaction solution is kept warm for 0.5 h after the gas of hydrochloride is inflated, and then cooled to the room temperature, standing for layering. The upper layer is organic layer while the lower layer is water layer. The water layer is dehydrated under vacuum and the gained ionic liquid can be recycled and used. The organic layer is transferred into a 500 ml four-neck flask and is rectified under vacuum. After desolventizing, 142.4 g 2,5-dimethylbenzyl chloride is finally provided (92.1% yield).

(2) Carbonylation and hydrolyzation reactions

To a 1000 ml autoclave, 77.3 g the said rectified 2,5-dimethylbenzyl chloride, 118.7 g pyridine, 0.6 g tetrakis(triphenylphosphine)palladium(0); 90 g water and 193.3 g isopropyl alcohol are added. Nitrogen is inflated to replace the air for three times and the temperature is raised to 70° C. At 70° C.~75° C., carbon monoxide is inflated until the pressure is not decreasing. After the reaction has finished, it is cooled to 40° C., then the pressure is relieved, and nitrogen is inflated to replace the air for three times again, the reaction solution is transferred into a 1000 ml four-neck flask and then 133.3 g 30% liquid caustic soda is added under the protection of nitrogen, which is stirred for 1 h at 60° C., then standing for layering. The upper layer is organic layer and the lower layer is water layer. 63.4 g 36% hydrochloric acid is added dropwise into the water layer until pH=1. The solution is kept warm for 1 h and filtered, dried under vacuum to give 71.3 g 2,5-dimethylphenylacetic acid (86.8% yield). Finally, small amount of heavy metal capture agent and flocculant can be added into the filtrate and filtered again to give the catalyst. The filtered catalyst can be recycled and reused.

The invention claimed is:

1. A method for preparing 2,5-dimethylphenylacetic acid, comprising:
    (1) producing 2,5-dimethylbenzyl chloride by performing a chloromethylation reaction comprising the following steps:
        mixing together p-xylene, a solvent ionic liquid, paraformaldehyde, and concentrated hydrochloric acid to obtain a first reaction mixture, wherein the mole ratio of the p-xylene, paraformaldehyde, and ionic liquid is 1:1.1-5:0.01-1;
        heating the first reaction mixture to a predetermined temperature;
        contacting the first reaction mixture with hydrogen chloride gas and allowing the chloromethylation reaction to proceed;
        maintaining the temperature of the reaction mixture at the predetermined temperature until 30 minutes after the reaction is completed;
        cooling the chloromethylation reaction solution, and allowing the reaction solution to layer into an organic layer and a water layer; and
        rectifying the organic layer under vacuum to obtain 2,5-dimethylbenzyl chloride; and
    (2) subjecting 2,5-dimethylbenzyl chloride to carbonylation and hydrolyzation reactions, comprising the following steps:
        adding to a reactor the 2,5-dimethylbenzyl chloride obtained from the chloromethylation reaction, an acid binding agent, and a catalyst to obtain a second reaction mixture;
        heating the second reaction mixture to a predetermined temperature;
        contacting the second reaction mixture with carbon monoxide gas and allowing the carbonylation and hydrolyzation reactions to proceed;
        after the reactions are completed, cooling the carbonylation and hydrolyzation reaction solution; and then adding liquid caustic soda to the cooled solution under a nitrogen atmosphere, and stirring;
        allowing the reaction solution to layer into an organic layer and a water layer;
        adjusting the pH of the water layer to a pH of 1; and then filtering the reaction solution to obtain 2,5-dimethylphenylacetic acid.

2. The method according to claim 1, wherein:
    in the chloromethylation reaction, the mole ratio of p-xylene, paraformaldehyde and ionic liquid is 1:1.1-2.0:0.01-0.5;
    in the chloromethylation reaction, the solvent is a substituted imidazole ionic liquid comprising an imidazole cation, and an anion selected from halogen ion, trifluoromethanesulfonate ion, tetrafluoroborate ion, and hexafluorophosphate ion;
    in the carbonylation and hydrolyzation reactions, the catalyst is selected from the group consisting of palladium chloride, palladium acetate, palladium sulfate, palladium nitrate, palladium oxide, dichlorodiamminepalladium, tetraammine dichloropalladium(II), tetrakis(triphenylphosphine)palladium(0), palladium(II)bis(triphenylphosphine) diacetate, palladium(II)bis(triphenyl- phosphine) dichloride, and palladium hydroxide;
    in the carbonylation and hydrolyzation reactions, the acid binding agent is selected from the group consisting of pyridine, triethylamine, alkali alcoholate, lithium alkylide, lithium amide, alkali hydroxide, alkali carbonate or bicarbonate, and acetate;
    in the carbonylation and hydrolyzation reactions, the solvent is selected from the group consisting of esters, ethers, alcohols, arenes, nitriles, and mixtures thereof.

3. The method according to claim 2, wherein:
    in the carbonylation and hydrolyzation reactions, the catalyst is tetrakis(triphenylphosphine)palladium(0), palladium(II)bis(triphenylphosphine) diacetate, or palladium(II)bis(triphenylphosphine) dichloride; and
    in the carbonylation and hydrolyzation reactions, the acid binding agent is pyridine or triethylamine.

4. The method according to claim 2, wherein the solvent of the carbonylation and hydrolyzation reactions is selected from the group consisting of methyl acetate, ethyl acetate, butyl acetate, ethyl ether, methyl t-butyl ether, tetrahydrofuran, p-dioxane, methanol, ethanol, isopropyl alcohol, tert-pentanol, benzene, toluene, chlorobenzene, acetonitrile, and propionitrile.

5. The method according to claim 4, wherein the solvent of the carbonylation and hydrolyzation reactions is isopropyl alcohol or tert-pentanol.

6. The method according to claim 1, further comprising:
    recovering the ionic liquid by dehydrating the water layer obtained from the chloromethylation reaction under vacuum so that the ionic liquid may be recycled and reused.

7. The method according to claim 1, further comprising:
   recovering the catalyst used in the carbonylation and hydrolyzation reactions by adding heavy metal capture agent and flocculant to a filtrate obtained in the filtering step, and refiltering the filtrate so that the catalyst may be recycled and reused.

* * * * *